United States Patent
Weber

(10) Patent No.: US 9,579,522 B2
(45) Date of Patent: Feb. 28, 2017

(54) LASER NEEDLE FOR PERFORMING A COMBINED LASER NEEDLE/ELECTRIC ACUPUNCTURE

(76) Inventor: Michael Weber, Lauenförde (DE)

(*) Notice: Subject to any disclaimer, the term of this patent is extended or adjusted under 35 U.S.C. 154(b) by 2748 days.

(21) Appl. No.: 11/648,643

(22) Filed: Jan. 3, 2007

(65) Prior Publication Data
US 2007/0129713 A1 Jun. 7, 2007

Related U.S. Application Data

(63) Continuation of application No. PCT/DE2005/001157, filed on Jun. 30, 2005.

(30) Foreign Application Priority Data

Jul. 3, 2004 (DE) .................... 10 2004 032 394

(51) Int. Cl.
A61B 18/18 (2006.01)
A61N 5/06 (2006.01)
(Continued)

(52) U.S. Cl.
CPC ........... *A61N 5/0619* (2013.01); *A61H 39/00* (2013.01); *A61H 39/08* (2013.01); *A61N 5/0622* (2013.01);
(Continued)

(58) Field of Classification Search
CPC .............. A61H 39/00; A61H 2039/005; A61H 2201/10; A61H 39/08; A61N 5/0619; A61N 2005/0645; A61N 2005/067; A61N 5/0622
(Continued)

(56) References Cited

U.S. PATENT DOCUMENTS 3,913,582 A   10/1975   Sharon .......................... 606/19
4,232,678 A   11/1980   Skovajsa ....................... 607/89
(Continued)

FOREIGN PATENT DOCUMENTS

DE   27 40 969      3/1979
DE   91 05 621.7   10/1991
(Continued)

OTHER PUBLICATIONS

Machine translation of D.E. 27 40 969.
(Continued)

*Primary Examiner* — David Shay
(74) *Attorney, Agent, or Firm* — Shlesinger, Arkwright & Garvey LLP

(57) ABSTRACT

Laser needle for performing a combined laser needle/electric acupuncture includes an optical fiber, the optical fiber being configured for transmitting a laser beam. Laser needle includes a current-conducting jacket, the current-conducting jacket being configured for surrounding the optical fiber, and the current-conducting jacket being configured for applying current-conducting stimulation current to tissue of a patient, in use, in addition to a laser beam being applied through the optical fiber, in use. A bottom end of the current-conducting jacket transitioning into a disk, the disk being configured for distributing the stimulation current on a larger area; and the disk being configured for simultaneously serving to attach the laser needle to the body of a patient, in use.

12 Claims, 2 Drawing Sheets

(51) Int. Cl.
*A61H 39/00* (2006.01)
*A61H 39/08* (2006.01)
*A61N 5/067* (2006.01)

(52) U.S. Cl.
CPC .... *A61H 2039/005* (2013.01); *A61H 2201/10* (2013.01); *A61N 2005/067* (2013.01); *A61N 2005/0645* (2013.01)

(58) Field of Classification Search
USPC ...................................... 607/88–93; 128/907
See application file for complete search history.

(56) References Cited

U.S. PATENT DOCUMENTS

| | | | |
|---|---|---|---|
| 4,479,496 A | 10/1984 | Hsu ................. | 606/189 |
| 4,653,495 A | 3/1987 | Nanaumi ............ | 606/16 |
| 4,779,593 A | 10/1988 | Kiernan ............. | 607/65 |
| 5,008,555 A | 4/1991 | Mundy .............. | 250/559.22 |
| 5,029,581 A | 7/1991 | Kaga et al. ......... | 607/89 |
| 5,094,242 A * | 3/1992 | Gleason et al. ...... | 600/377 |
| 5,131,409 A | 7/1992 | Lobarev et al. ...... | 607/156 |
| 5,193,526 A | 3/1993 | Daikuzono .......... | 606/15 |
| 5,304,207 A | 4/1994 | Stromer et al. | |
| 5,358,503 A | 10/1994 | Bertwell et al. ..... | 606/27 |
| 5,375,596 A | 12/1994 | Twiss et al. ........ | 600/424 |
| 5,514,168 A | 5/1996 | Friedman ........... | 607/89 |
| 6,074,411 A | 6/2000 | Lai et al. | |
| 6,306,160 B1 * | 10/2001 | Nidetzky ............ | 607/89 |
| 6,513,962 B1 | 2/2003 | Mayshack et al. .... | 362/583 |
| 6,572,637 B1 | 6/2003 | Yamazaki et al. .... | 607/89 |
| 6,594,434 B1 | 7/2003 | Davidson et al. ..... | 385/135 |
| 6,916,329 B1 * | 7/2005 | Zhao ............... | 128/907 |
| 7,179,278 B2 | 2/2007 | Schikora ........... | 607/89 |
| 7,751,895 B2 * | 7/2010 | Jones et al. ........ | 607/46 |
| 8,043,348 B2 | 10/2011 | Weber | |
| 2004/0092859 A1 | 5/2004 | Schikora | |
| 2004/0176825 A1 | 9/2004 | Vaynberg et al. .... | 607/89 |
| 2005/0049653 A1 * | 3/2005 | Wang ............... | A43B 1/0054 |
| | | | 607/48 |
| 2007/0260297 A1 | 11/2007 | Chariff ............. | 607/89 |

FOREIGN PATENT DOCUMENTS

| | | |
|---|---|---|
| DE | 295 19 433 U1 | 3/1996 |
| DE | 203 09 976 U1 | 10/2003 |
| EP | 0 495 757 A1 | 7/1992 |
| EP | 1 337 298 B1 | 8/2003 |
| WO | 02/40098 A1 | 3/2002 |
| WO | 2005/009538 A2 | 2/2005 |

OTHER PUBLICATIONS

International Search Report dated Jan. 5, 2005 in PCT application No. PCT/DE2004/000960, filed May 7, 2004 (3 pages).
International Search Report dated Jan. 5, 2005 in PCT application No. PCT/DE2004/000960, filed May 7, 2004 (2 pages).
International Search Report dated Jan. 9, 2007 in PCT application No. PCT/DE2005/001157, filed Jun. 30, 2005 (7 pages).

* cited by examiner

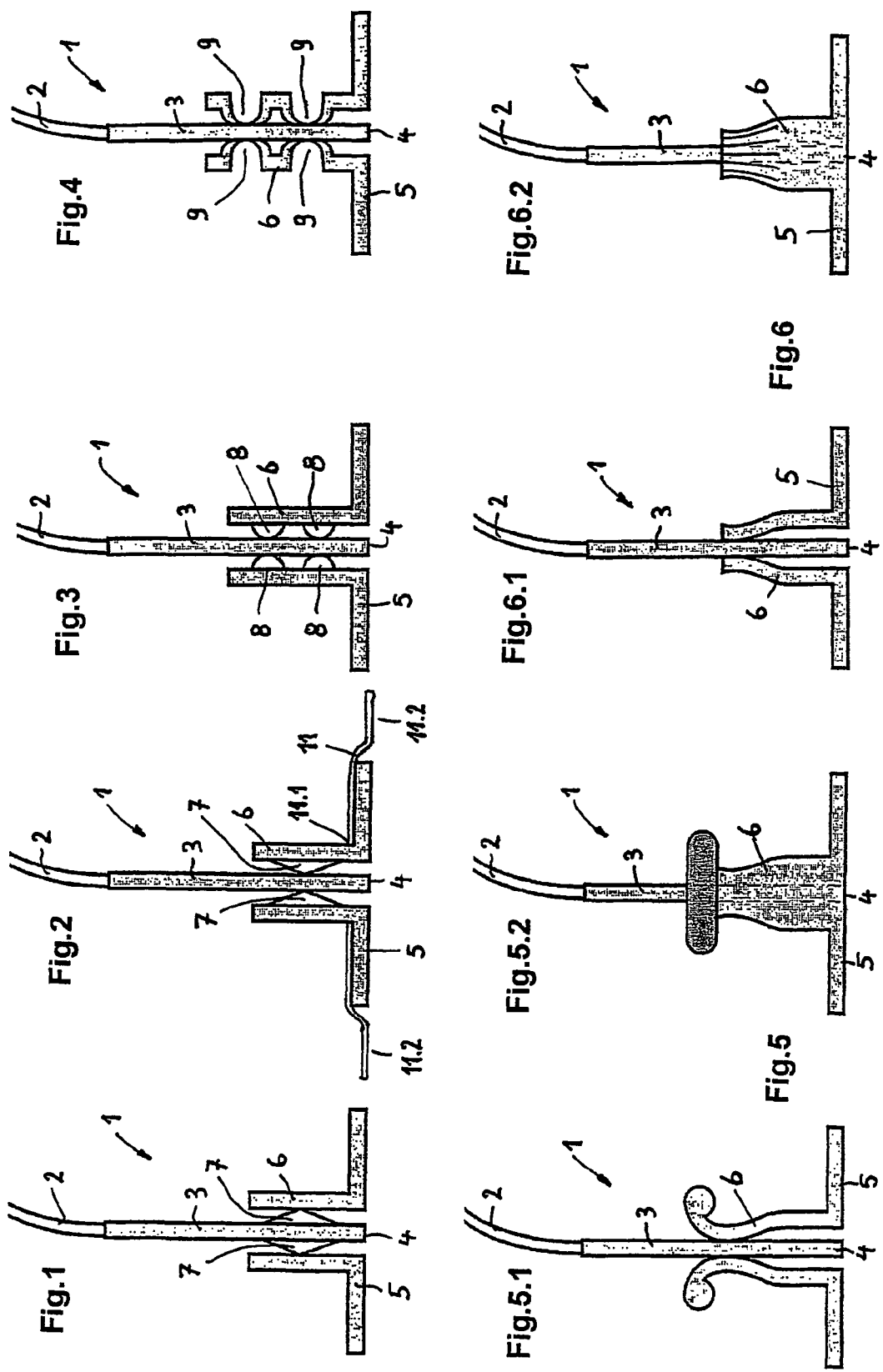

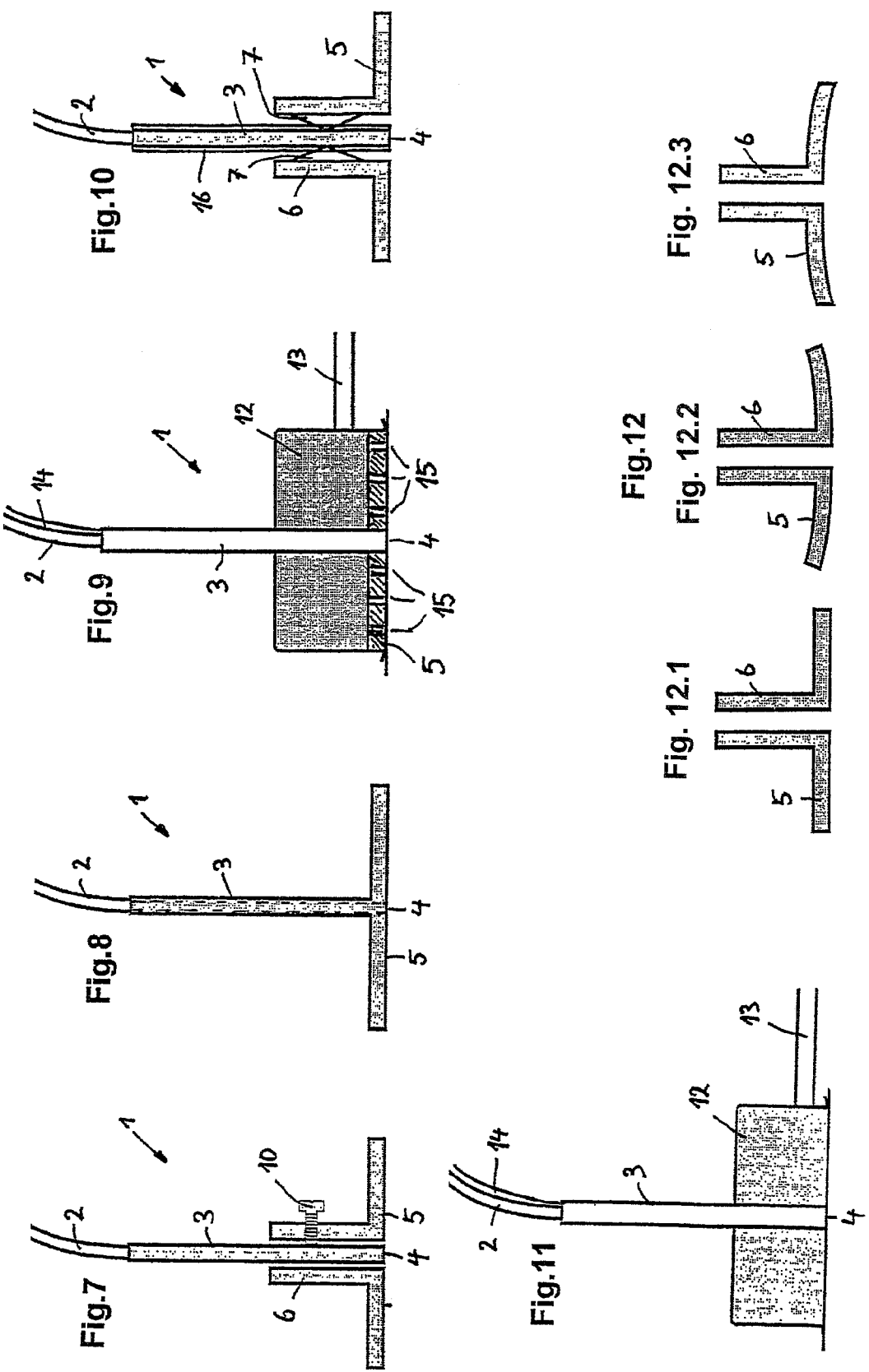

LASER NEEDLE FOR PERFORMING A COMBINED LASER NEEDLE/ELECTRIC ACUPUNCTURE

CROSS-REFERENCE TO RELATED APPLICATIONS

This application is a continuation of application no. PCT/DE2005/001157, filed 30 Jun. 2005, which claims the priority of German application no. 10 2004 032 394.1, filed Jul. 3, 2004, and each of which is incorporated herein by reference.

FIELD OF THE INVENTION

The present invention relates to a laser needle. More particularly, the invention relates to a laser needle for performing a combined laser needle/electric acupuncture that includes an optical fiber, the optical fiber being configured for transmitting a laser beam.

BACKGROUND OF THE INVENTION

A generic laser needle is known from DE 203 09 976 U1. This utility model describes a new device for acupuncture using laser radiation. With this device, as in all other known devices for laser acupuncture, the end pieces, the so-called laser needles, must be brought into direct contact with the skin of the patient in order to permit the laser radiation to be optimally directed into the tissue. This ensures a high energy density at the acupuncture point.

The abovementioned utility model also describes a laser needle for combined laser needle/electric acupuncture. This laser needle includes an optical fiber, e.g. a glass fiber or a glass-fiber-analog plastic fiber, which is surrounded by a current-conducting jacket. In addition to the laser beam brought into the tissue via the optical fiber, stimulation current is transmitted into the skin or tissue of a patient via this jacket. In the professional world, this laser needle has come to be known under the name "Weber needle."

Another device for acupuncture using laser radiation is described in EP 1 337 298 A1. The laser needle used in connection with this device is not suitable for electric acupuncture. An attachment element which can be displaced on the housing of the laser needle is provided for attaching the laser needle to the body of a patient. In the disclosed embodiment, it consists of a shaft, which can be pushed onto the housing of the laser needle and transitions into a disk at its lower end. The attachment element consists of rubber and is held on the laser needle by static friction between the shaft and the housing. In another embodiment, a clamp fastens the attachment element to the laser needle. Arranged on the bottom side of the disk is a double acting adhesive ring, which is used to attach the attachment element and thereby the laser needle to the body of a patient.

It has been scientifically proven that both laser needle acupuncture and also electric acupuncture on specific points of the human body produce detectable changes in the nervous system (improvement in oxygen supply, of blood flow, and of metabolic activity). It can therefore be assumed that application of laser light combined with stimulation current at multiple points simultaneously will bring about a considerably augmented effect in treatment and thereby a substantial improvement in the therapeutic effectiveness of the system used. Combined laser needle/electric acupuncture is therefore of considerable relevance to medical policy and health policy.

OBJECTS AND SUMMARY OF THE INVENTION

Given this background, it is an object of the present invention to yet improve the efficiency of the known laser needle for combined laser needle/electric acupuncture.

This object is achieved according to the invention with a laser needle for performing a combined laser needle/electric acupuncture that includes an optical fiber, the optical fiber being configured for transmitting a laser beam. The laser needle includes a current-conducting jacket, the current-conducting jacket being configured for surrounding the optical fiber, and the current-conducting jacket being configured for applying current-conducting stimulation current to tissue of a patient, in use, in addition to a laser beam being applied through the optical fiber, in use. A bottom end of the current-conducting jacket transitioning into a disk, the disk being configured for distributing the stimulation current on a larger area; and the disk being configured for simultaneously serving to attach the laser needle to the body of a patient, in use.

In one advantageous development of the invention, the disk can either be of one-piece construction with the jacket, or else be provided with a shaft which can slide over the jacket and be fixed to it with a force-fit or form-fit and be current-conducting.

The wider bearing surface of the disk has the advantage over the known laser/electric acupuncture needle that the stimulation current is distributed over a large area on the tissue. Higher current doses can be supplied via the large bearing surface without overheating the tissue. Moreover, the effectiveness of the stimulation current flow on the skin and likewise the acupuncture effect is significantly increased if a substantially larger surface support exists. To this end, the effectiveness of the current's penetration into the skin can be increased even more by placing a conducting liquid or a conducting gel between the bottom side of the disk and the skin.

The disk simultaneously serves to attach the laser needle to the body of a patient. Accordingly, several possibilities exist for this.

In one embodiment of the invention, the needle is attached using a perforated bandage whose hole can be pushed over one or both of the jacket and shaft of the disk, respectively, so that the bandage rests on the disk from above and its adhesive layer protrudes from the disk laterally. The adhesive surfaces, which are thereby relatively distant from the longitudinal axis of the laser needle, and the relatively large bearing area of the disk provide for a secure attachment of the laser needle on the skin of a patient.

In another embodiment of the invention, the laser needle is attached to the body of a patient by a negative pressure; i.e., a vacuum. To this end, the disk is perforated and equipped with an attached suction cup which can be evacuated via a suction line to generate the vacuum.

It goes without saying that these attachment possibilities with a perforated bandage and a suction cup are transferable to simple laser needles, that is to say, to laser needles with which electric acupuncture cannot be performed.

In a development of the invention, it is furthermore advantageous for the disk and its shaft to include high-grade steel, such as stainless steel. This material not only guarantees good conduction of current, but it can be sterilized in a steam or hot air sterilizer following treatment and reused. This ensures optimum hygiene for the acupuncture treatment.

Further developments of the invention are set forth below. The invention will now be explained in more detail based on exemplary embodiments. The associated drawings schematically show various inventive embodiments.

BRIEF DESCRIPTION OF THE DRAWINGS

FIG. 1 shows an embodiment according to the invention in which the disk is clamped to the laser needle via its shaft and spring element;

FIG. 2 is a further embodiment according to the invention in which the disk is clamped to the laser needle via its shaft and spring element;

FIG. 3 is a still further embodiment according to the invention in which the disk is clamped to the laser needle via its shaft and spring element;

FIG. 4 is another embodiment according to the invention in which the disk is clamped to the laser needle via its shaft and spring element;

FIG. 5.1 is a further embodiment according to the invention in which the disk is clamped to the laser needle via its shaft and spring element;

FIG. 5.2 shows another embodiment according to the invention in which the disk is clamped to the laser needle via its shaft and spring element;

FIG. 6.1 shows another embodiment according to the invention in which the disk is clamped to the laser needle via its shaft and spring element;

FIG. 6.2 shows a still further embodiment according to the invention in which the disk is clamped to the laser needle via its shaft and spring element;

FIG. 7 shows an attachment of the disk to the laser needle by use of a threaded connection;

FIG. 8 shows a disk of one-piece construction with the current-conducting jacket of the laser needle;

FIG. 9 shows a development with a suction cup attached on the disk;

FIG. 10 is an illustration according to FIG. 2 with reduced current-application area;

FIG. 11 is an illustration according to FIG. 9 with reduced current-application area;

FIG. 12 shows various disk shapes:

FIG. 12.1 shows an embodiment in which the disk is shaped straight;

FIG. 12.2 shows a still further embodiment in which the disk is shaped convex; and FIG. 12.3 shows an embodiment in which the disk is shaped concave.

DETAILED DESCRIPTION OF THE INVENTION

Devices for performing combined laser needle/electric acupuncture include end pieces, so-called laser needles 1 which possess an optical fiber 2 and a current-conducting metal jacket 3 which surrounds the optical fiber. A laser beam, which the optical fiber 2 optimally carries into the tissue directly through its output region 4 on a bottom end facing the skin of a patient, is directed into the optical fiber 2 via a laser diode (not illustrated), the output region being in direct contact with the skin (not illustrated) of a patient. The optical fiber 2 is located in a protective plastic jacket, which simultaneously carries a supply lead to the power supply of the jacket 3. To this extent, the laser needle 1 described up to this point corresponds to the laser/electric acupuncture needle known from the prior art.

To increase the efficiency of laser/electric acupuncture needles and to improve the attaching of these types of needles to the body of a patient, there are provided disks 5, which distribute the stimulation current for the electric acupuncture over a larger area. Disks 5 are straight and have a bottom face facing the skin of a patient and the bottom face of the disk and the bottom face of the output region of the optical fiber are flush, in other words, in the same line, or in the same plane, as shown.

The optical fiber 2, which carries the laser into the tissue directly through its output region 4, has a cross-sectional area, as will be readily apparent to a person having ordinary skill in the art, and as may be appreciated from the Figs. Further, output region 4 of optical fiber 2 has a cross-sectional area, which is the same cross-sectional area, as will likewise be readily apparent to a person having ordinary skill in the art, and as may be appreciated from the Figs.

In the embodiments according to FIGS. 1 to 7, 10, and 12, a shaft 6, which serves to attach the disk 5 to the jacket 3 of the laser needle 1, is of one-piece construction with the disk 5. In the exemplary embodiments according to FIGS. 1 to 6, the attachment is accomplished via spring element, which simultaneously produces a current-conducting connection between the jacket 3 and the disk 5. In the case of the exemplary embodiment according to FIG. 1, the spring tongues 7 are of one-piece construction with the jacket 3. When the shaft 6 is pushed onto the jacket 3, these spring tongues 7 deflect somewhat and then clamp the shaft 6, and thereby also the disk 5, to the jacket 3 on the basis of the spring pressure. In the exemplary embodiment according to FIG. 2, the spring tongues 7 are configured on the shaft 6, in a reversal of the preceding example.

FIGS. 3 to 6 show additional variants in which the shaft 6 is attached to the jacket 3 by spring pressure. In the case of the exemplary embodiment according to FIG. 3, spring-mounted balls 8 in the shaft 6 provide the necessary pressure. In the example according to FIG. 4, the shaft 6 is provided with indentations 9, via which the necessary spring pressure is provided.

In the exemplary embodiments according to FIGS. 5 and 6, in which FIGS. 5.1 and 6.1 show longitudinal sections and FIGS. 5.2 and 6.2 show full illustrations, the upper ends of the shafts 6 are pulled inwards so that a springy clamping effect also results here.

In the exemplary embodiment shown in FIG. 7, the shaft 6 is attached to the jacket 3 by use of a set screw 10. Here too, the set screw 10 produces an electrically conducting connection to the jacket 3.

FIG. 8 shows an embodiment in which the jacket 3 and disk 5 are of one-piece construction.

In the embodiments of the invention described above, the laser needle 1 is attached to the body of a patient by use of a perforated bandage 11, which is only shown in FIG. 2 for the sake of example. The perforated bandage 11 with its central hole 11.1 is pulled over the shaft 6 and then rests on the disk 5 from above, the edges 11.2 of the perforated bandage 11, which project over the disk 5, serving for sticking to the skin of a patient. The wide base of the disk 5 and the fact that the adhesive joints 11.2 are located relatively distant from the central axis of the laser needle 1 in the lateral direction guarantee that the laser needle 1 will be securely attached to the human body.

The exemplary embodiment according to FIG. 9 represents another attachment possibility for a laser needle 1. Here, in connection with the embodiment according to FIG. 8, a suction cup 12 is attached to the upper surface of the disk 5. This suction cup 12 is evacuated by suction lines 13, 14, wherein the suction line 14 is brought into the suction cup 12 with the optical fiber 2 from above, while the suction line 13 is introduced into the suction cup 12 separately. In the exemplary embodiment according to FIG. 9, both suction lines 13, 14 are sketched in at the same time. It goes without saying that only one of these suction lines 13, 14 will be used in practice at a time. The disk 5 has perforations in the form of through-holes 15, through which the vacuum produced in the suction cup acts on the skin of a patient and thereby sucks on the skin for secure suction of the disk 5.

FIG. 11 shows a variant of the embodiment according to FIG. 9. In this variant, the stimulation current is supplied only via the small end face of the jacket 3. This stimulation current application is expedient if it is necessary to produce a higher current flow on a smaller area in particular applications. In this example too, the two suction lines 13, 14 are both illustrated for sake of example.

The development according to FIG. 10 is a variation of the exemplary embodiment shown in FIG. 2. Here a plastic sleeve 16, which electrically insulates the shaft 6 and therefore the disk 5 from the current-conducting jacket 3, is pulled over the jacket 3. The application of stimulation current in this variant therefore corresponds to that in the exemplary embodiment according to FIG. 11.

FIG. 12 illustrates various shapes of the disk 5 in order to guarantee an optimal adaptation of body shapes. Thus the disk 5 can be shaped straight as shown in FIG. 12.1, convex as shown in FIG. 12.2, or also concave as shown in FIG. 12.3. Here it can be expedient to provide a treating physician with an assortment of these types of disks, so that a disk of a proper and/or desired shape depending on the acupuncture point can be selected.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

The invention claimed is:

1. Laser needle for performing a combined laser needle/electric acupuncture, comprising:
    a) an optical fiber, the optical fiber having a cross-sectional area, and having a bottom end including an output region with the same cross-sectional area, and being configured for transmitting a laser beam;
    b) a current-conducting jacket, the current-conducting jacket being configured for surrounding the optical fiber, and the current-conducting jacket being configured for applying current-conducting stimulation current to tissue of a patient, in use, in addition to a laser beam being applied through the optical fiber, in use;
    c) a bottom end of the current-conducting jacket fixed to a disk including a current-conducting material, the disk being straight and having a bottom face and being configured for distributing the stimulation current on a larger area;
    d) the bottom face of the disk and the bottom end of the optical fiber being flush; and
    e) the disk being configured for simultaneously serving to attach the laser needle to the skin of the body of a patient, in use.

2. Laser needle according to claim 1, wherein:
    a) the disk is of one-piece construction with the current-conducting jacket.

3. Laser needle according to claim 1, wherein:
    a) the disk is provided with a shaft and the shaft and the disk include a high-grade steel.

4. Laser needle according to claim 1, wherein:
    a) the disk is provided with a shaft; and
    b) a perforated bandage, which is provided with a hole and which includes an adhesive layer, laterally protrudes from the disk, and can be pushed over the jacket and the shaft to attach the laser needle.

5. Laser needle according to claim 1, wherein:
    a) the disk is perforated and includes an attached suction cup, which can be evacuated via a suction line, to induce a vacuum.

6. Laser needle according to claim 1, wherein:
    a) the laser needle has a longitudinal axis;
    b) the disk is provided with a shaft; and
    c) a perforated bandage, which is provided with a hole and which includes an adhesive layer having an adhesive surface, and the adhesive layer and adhesive surface laterally protrude from the disk and are thereby distant from the longitudinal axis of the laser needle, and can be pushed over the jacket and the shaft to attach the laser needle.

7. Laser needle according to claim 1, wherein:
    a) the disk is fixed to the current-conducting jacket with a form-fit.

8. Laser needle according to claim 7, wherein:
    a) the disk is provided with a shaft; and
    a) the shaft and the disk include a stainless steel.

9. Laser needle according to claim 1, wherein:
    a) the disk is fixed to the current-conducting jacket with a force-fit.

10. Laser needle according to claim 9, wherein:
    a) the disk is provided with a shaft; and
    a) the shaft and the disk include a stainless steel.

11. Laser needle according to claim 9, wherein:
    a) the disk fixed to the current-conducting jacket with a force-fit is fixed by a spring element.

12. Laser needle according to claim 11, wherein:
    a) the spring element includes a spring tongue.

* * * * *